United States Statutory Invention Registration [19]

[11] Reg. Number: H669

Fairchild et al. [43] Published: Sep. 5, 1989

[54] SAMARIUM-145 AND ITS USE AS A RADIATION SOURCE

[75] Inventors: Ralph G. Fairchild, Setauket; Brenda H. Laster, Plainview; Samuel Packer, Great Neck, all of N.Y.

[73] Assignee: The United States of America as represented by the United States Department of Energy, Washington, D.C.

[21] Appl. No.: 938,839

[22] Filed: Dec. 8, 1986

[51] Int. Cl.[4] ..... A61N 5/12
[52] U.S. Cl. ..... 600/3; 424/1.1
[58] Field of Search ..... 128/1.1, 1.2; 424/1.1

[56] References Cited

U.S. PATENT DOCUMENTS

| | | | |
|---|---|---|---|
| 4,434,788 | 3/1984 | Nakatsugawa et al. . | |
| 4,445,225 | 4/1984 | White | 250/271 |
| 4,510,924 | 4/1985 | Gray | 128/1.2 |
| 4,566,114 | 1/1986 | Watt et al. | 378/88 |
| 4,702,228 | 10/1987 | Russell et al. | 128/1.2 |

OTHER PUBLICATIONS

Fairchild et al, Workshop on Photon Activation Therapy, BNL Report 51997, Apr. 18, 1985.

Fairchild et al, "Photon Activation Therapy", Strahlentherapie, 160, 1984, pp. 758–763.

Fairchild et al, Investigative Radiology, Jul.–Aug., 1982, vol. 17, No. 4, pp. 407–415.

*Primary Examiner*—Teddy S. Gron
*Assistant Examiner*—Richard Treanor
*Attorney, Agent, or Firm*—Margaret C. Bogosian; Thomas G. Anderson; Judson R. Hightower

[57] ABSTRACT

The present invention covers a new radiation source, samarium-145, with radiation energies slightly above those of I-125 and a half-life of 340 days. The samarium-145 source is produced by neutron irradiation of SM-144. This new source is useful as the implanted radiation source in photon activation therapy of malignant tumors to activate the stable I-127 contained in the IdUrd accumulated in the tumor, causing radiation sensitization and Auger cascades that irreperably damage the tumor cells. This new source is also useful as a brachytherapy source.

1 Claim, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SAMARIUM-145 AND ITS USE AS A RADIATION SOURCE

The U.S. Government has rights in this invention pursuant to Contract Number DE-AC02-76CH00016, between the U.S. Department of Energy and Associated Universities Inc.

BACKGROUND OF THE INVENTION

Radiotherapy has been a widely used therapeutic approach to the treatment of various forms of cancer. However, although radiotherapy certainly has marked an advancement in the treatment of cancer, its imprecision and toxic side effects require that further improvements be made in this therapeutic approach. The major problems presented by radiotherapy are imprecise beam alignment, arising in large part because of equipment limitations, as well as incomplete knowledge of the microscopic distribution of tumor, and radioresistance of poorly oxygenated cells lying in poorly vascularized tumor regions. Imprecise beam alignment, coupled with the difficulty of locating microscopic fingers of tumor growth in order to include these fingers within the treatment region, and the toxic effects of the radiation on the surrounding healthy tissue lead in many instances to therapeutic failure using traditional radiation therapy.

Recent investigations have focused on two approaches to radiation therapy that are intended to overcome some of the limitations of traditional radiotherapy. One such approach involves photon activation therapy (PAT) and the other involves brachytherapy. Applicants have been involved in the development of both of these approaches. The first of these approaches, PAT, is a technique in which the thymidine analog 5'-iodo-2'-deoxyuridine (IdUrd), wherein the iodine is stable $^{127}I$, is administered to a patient with a malignant tumor. As the IdUrd circulates through the body, cells that are dividing and therefore manufacturing DNA incorporate some of the IdUrd into their DNA in place of thymidine. The IdUrd settles primarily in the cells of the tumor because of the rapid cell proliferation in the tumor. The IdUrd itself possesses anticancer activity in that it sensitizes the tumor cells to the lethal effects of photon irradiation.

After the IdUrd has accumulated in the tumor, it is activated with external photons to produce a cytotoxic response in the tissue due to radiation sensitization and the production of high Linear Energy Transfer (LET) radiation in the form of Auger electron distributions (Auger cascades) generated through photoactivation of the stable iodine incorporated in the tumor cell in the IdUrd. The photoactivation can be provided by an external source of x-rays or by an implanted radiation source. PAT has the advantage of combining the anticancer and radiosensitization effects of IdUrd with the high Linear Energy Transfer radiations provided by Auger electrons induced in the iodine. Accumulations of the IdUrd in the tumor permits delivery of high radiation selectively to tumor, with the surrounding normal tissue being traversed by the low energy activating photons and thus suffering little damage. The PAT approach seems to have the most clinical potential in the treatment of tumors of the brain, head and neck.

The second new approach to the use of radiation therapy in the treatment of malignant tumors is brachytherapy, which is radiotherapy in which the source of irradiation is placed close to the surface of the body or within the body cavity. Several radioiosotopic sources are now widely used in the treatment of cancer using brachytherapy; they are $^{226}Ra$, $^{60}Co$, $^{198}Au$, $^{192}Ir$ and $^{125}I$. These brachytherapy sources are employed for intracavitary, interstitial and superficial therapy of localized tumors. Of these radioisotopic sources, $^{125}I$ is probably the most interesting clinically for several reasons. Iodine's lower energy photons show relatively rapid attenuation, resulting in lower doses to normal tissue outside the treatment area. Also, iodine's lower energy photons permit small amounts of high-Z-material, such as gold or lead foils, to provide almost complete energy absorption and thus gold or lead foil plaques can be used to shield vital body tissue or organs from the photons.

Applicants have now developed a new radioisotopic source, samarium-145 ($^{145}Sm$), which has important applications in both photon activation therapy and brachtherapy.

DETAILED DESCRIPTION OF THE INVENTION

Figure 1:
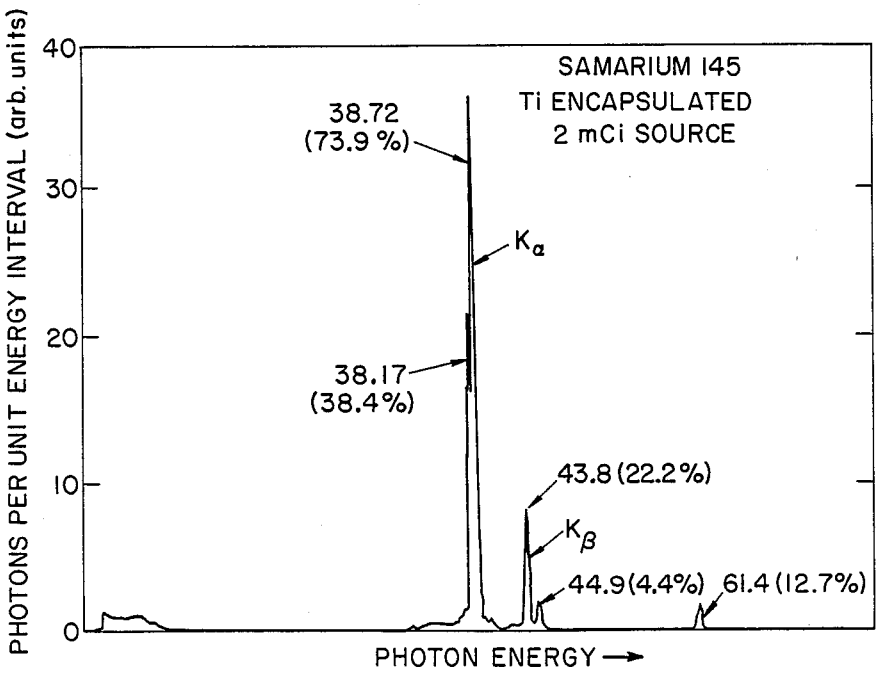
FIG. 1 defines the photon energy spectrum from a titanium encapsulated $^{145}Sm$ source measured with a Ge detector.

Applicants have produced a new radiation source, $^{145}Sm$. Samarium-145 has a half-life of 340 days and emits photons with energies from 38 to 61 keV. Decay is by electron capture to $^{145}Pm$ ($T_{\frac{1}{2}}$17.7 years) which emits x-rays of similar energies. Decay results in 140 x-rays per 100 disintegrations in the energy region between 38–45 keV, plus 13 $\gamma$-rays at 61 keV. These photon energies are slightly above those of I-125.

The $^{145}Sm$ source is produced by neutron irradiation of enriched Sm-144. Twenty-day irradiations at the High Flux Beam Reactor (HFBR) at Brookhaven National Laboratory in a flux density in the range of $5.5\times10^{14}$ n/cm$^2$-sec. have produced approximately 1.5 mCi of Sm-145 per milligram of $Sm_2O_3$. Higher activity sources can be produced by extended irradiations or by irradiating samarium metal. When produced by neutron irradiation of enriched $^{144}Sm$, contaminations of $^{154}Eu$ and $^{155}Eu$ were less than 2%.

These Sm-145 sources can be encapsulated in needle-sized capsules or seeds for surgical implantation directly into the tumor or into the region of the tumor. This implantation permits the Sm-145 source to act itself as the radiation source in brachytherapy. In the alternative, implantation of the Sm-145 source could permit its use as the source of activating photons to activate the iodine-27 used in IdUrd-photon activation therapy. If used as a brachytherapy source in the treatment of ocular or brain tumors, the Sm-145 source can be encapsulated in a titanium tube, having a dimension of about 0.8 mm$\times$4 mm. The dose rate of the implanted Sm-145 source is approximately 0.8 rad/hr ·mCi at 1 cm in tissue, with negligible high energy contaminations.

The HVL of the $^{145}Sm$ photon component with energies greater than 10 keV is 0.06 mm of lead, compared to 0.025 mm for $^{125}I$, but much smaller than that of the higher energy brachytherapy sources (12 mm in the case of $^{60}Co$). This characteristic greatly facilitates the transportation and storage of $^{145}Sm$ sources and simplifies the protection of medical staff as well as the general public. Further, radiation fields around plaques or molds can be confined so that sensitive tissue can be protected.

The low energy photons from Sm-145 provide advantages from the standpoint of radiation protection which are similar to $^{125}I$. Dose distributions from source arrays should be more homogeneous then $^{125}I$, with the additional benefit of a significantly extended shelf-life, resulting from the 340 day half-life of $^{145}Sm$ compared to the 60 day half-life of $^{125}I$.

Comparison of the characteristics of the new $^{145}Sm$ source with the characteristics of the widely used $^{125}I$ source shows that the Sm-145 source should be useful for almost any conventional brachytherapy application.

Another important characteristic of $^{145}Sm$ is that the photons emitted have energies just above the K absorption edge of iodine (33.2 keV). These sources thus can provide low energy photons with energies appropriate for maximizing possible radiation enhancement with the thymidine (Thd) analog iodinated deoxyuridine (IdUrd) when this drug is used in photon activation therapy. Stimulating Auger cascades with photons above the K absorption edge of iodine can augment the effects of radio-sensitization. Protracted irradiation times using a Sm-145 source implanted for between four and forty days should selectively induce non-repairable damage in tumors via radiation sensitization and photon activation of Auger cascades. Photon activation therapy may be of most value in the treatment of brain tumors, since the central nervous system does not synthesize DNA.

IdUrd does not accumulate in normal brain tissue and therefore only the tumor and not the surrounding normal tissue will become radiosensitized by the iodine and damaged by the Auger cascades.

EXAMPLE 1

Preparation of Samarium-145

The $^{144}Sm$ was obtained from the Isotope Sales Department of Oak Ridge National Laboratory, Oak Ridge, Ten 37831. The $^{144}Sm$ routinely has small contaminations of other Sm isotopes. Table 1 below shows an isotope analysis of one of the Sm-144 samples received from Oak Ridge which was used in the preparation of Sm-145.

TABLE 1

Isotopic Analysis of Samarium-144 (Sample XXXX)

| Isotope | Atomic Percent | Precision |
|---|---|---|
| Samarium-144 | 96.47 | ±0.05 |
| 147 | 1.08 | ±0.01 |
| 148 | 0.56 | ±0.01 |
| 149 | 0.54 | ±0.01 |
| 150 | 0.24 | ±0.01 |
| 152 | 0.65 | ±0.01 |
| 154 | 0.46 | ±0.01 |
| Europium | <0.005 | |

Irradiations were carried out at Brookhaven National Laboratory's High Flux Beam Reactor (HFBR) at the V-12 reflector irradiation tube at a thermal neutron fluence rate of $3.8\times10^{14}$ n/cm$^2$-sec and a fast fluence rate (>1 MeV) of $8.3\times10^{11}$ n/cm$^2$-sec. Following an irradiation of 26.5 days ($8.7\times10^{20}$ n/cm$^2$), 56 MBq $^{145}Sm$ was produced per mg $^{144}Sm$ (~112MBq, or 3 mCi/source).

Samarium-145 decays by electron capture to $^{145}Pr$, which in turn decays by the same mechanism to $^{145}Nd$ (stable). The corresponding photon energies and abundances are given in Table 2.

EXAMPLE 2

Preparation of the Sm-145 Sources

An eye-plaque was fabricated, with 90 mg $^{144}Sm$ metal, and irradiated to produce ~200 mCi of $^{145}Sm$; this source is suitable for use with ocular tumors. In addition, a number of Sm sources have been produced analogous to the small $^{125}I$ "seeds" (0.5–40 mCi) available commercially from 3-M Company, Medical-Surgical Division, St. Paul, Minn. 55144.

TABLE 2

Photon Energies and Abundances

| $^{145}Sm$ and $^{145}Pm$ | | | | | | Possible Contaminants | | | | | |
|---|---|---|---|---|---|---|---|---|---|---|---|
| $^{145}Sm$ ($T_{\frac{1}{2}}$ = 340 days) (electron capture) | | | $^{145}Pm$ ($T_{\frac{1}{2}}$ = 17.7 yr) (electron capture) | | | $^{145}Eu$ ($T_{\frac{1}{2}}$ = 8.5 y) $\beta^-$ (MeV) = 1.86 (12%) 0.89 (23%); 0.59 (45%) | | $^{155}$($T_{\frac{1}{2}}$ = 4.96 y) $\beta^-$ (MeV) = 0.25 (16%); 0.15 (84%) | | $^{156}$ Eu ($T_{\frac{1}{2}}$ = 15.2 d) $\beta^-$ (MeV) = 2.43 (33%); 1.19 (14%); 0.49 (36%) | |
| Photon Energy (keV) | | Photons per Disintegration | Photon Energy (keV) | | Photons per Disintegration | Photon Energy (keV) | Photons per Disintegration | Photon Energy (keV) | Photons per Disintegration | Photon Energy (keV) | Photons per Disintegration |
| X-ray | 38.2 | 0.384 | X-ray | 36.9 | 0.211 | 43 | 0.131 | 43 | 0.129 | 43 | 0.065 |
| X-ray | 38.7 | 0.739 | X-ray | 37.4 | 0.386 | 123 | 0.405 | 86 | 0.327 | 89 | 0.09 |
| X-ray | 43.8 | 0.222 | X-ray | 42.2 | 0.122 | 723 | 0.197 | 105 | 0.21 | 646 | 0.07 |
| X-ray | 44.9 | 0.044 | X-ray | 43.3 | 0.025 | 873 | 0.113 | | | 811 | 0.10 |
| γ-ray | 61.4 | 0.127 | γ-ray | 67.2 | 0.007 | 996 | 0.107 | | | 1065 | 0.05 |
| | | 1.516 | γ-ray | 72.4 | 0.022 | 1005 | 0.176 | | | 1153 | 0.07 |
| | | | | | 0.773 | 1275 | 0.355 | | | 1154 | 0.05 |
| | | | | | | | | | | 1230 | 0.09 |
| | | | | | | | | | | 1242 | 0.07 |

These sources have been constructed primarily for stereotactic implantation in brain tumors, although they could be used for other conventional brachytherapy applications. Small titanium tubes (~4.5 by 0.8 mm; wall thickness 0.05 mm) have been loaded with ~2 mg of $Sm_2O_3$ (96.5% enriched $^{144}Sm$) and then laser welded in a procedure approved for human use with palladium-103 sources. The available volume (0.7 mm IDx 3.2 mm L) provides an effective density of ~1.3 g Sm/cm$^3$ which could be increased by ~5.8× if Sm metal were used.

In brachytherapy, source strength is usually specified in terms of air kerma rate at one meter from the center of the source, along the perpendicular bisector. The absolute calibration of Sm seeds with conventional ionization chamber techniques presents problems because of: (1) the relative low energy of the photons emitted upon $^{145}$Sm decay; (2)$\beta-$ particles from the $^{154}$Eu contamination; (3) Ti K-x-rays, and; (4) the low activity of the seeds. For this reason the calibration of each seed is accomplished by comparing the intensity of the 61.4 keV $\gamma$-rays from $^{145}$Sm with that of the 59.54 keV $\gamma$-rays from a calibrated $^{241}$Am source. The average branching ratio of 12.6% was obtained by averaging the values of 12.7% and 12.45% obtained from Erdtmann, et al., "The Gamma Rays of the Radionuclides", (Weinheim-New York: Verlag, Chemise) and Lederer, et al., "1978 Tables of Isotopes" (7th Ed.) (New York: I. Wiley and Sons, Inc.) respectively. A Ge detector in a standard geometric configuration (50 cm source-detector distance) was used. Due to practical considerations, the activity is stated as the apparent activity of $^{145}$Sm. Calibrated sources with higher energy photons, such as $^{133}$Ba and $^{152}$Eu, were used to determine spectroscopically the concentrations of $^{154}$Eu and $^{155}$Eu impurities (less than 2% in both cases). Using these figures, the air kerma rate constant of the seed due to photons of energy greater than 10 keV, has been calculated to be 0.775 rad cm$^2$mCi$^{-1}$h$^{-1}$.

EXAMPLE 3

Determining Dosimetry of the Sm-145 Sources Calculated Dose Distribution

The radial distribution of absorbed dose rate around a $^{145}$Sm seed in a "tissue equivalent" A-150 plastic infinite phantom was calculated with the following method. The source was simulated by a regularly spaced linear array of point sources of equal activity. The contribution of each source to the absorbed dose rate at each location was calculated using Berger's method for point sources in infinite isotropic media [Berger, 1968 MIRD Pamphlet 2, *J. Nucl. Med.*, Suppl. 1, 15-25 (1968)]. The absorbed dose rate was corrected for self-absorption in the seed according to the path length in the seed. Because of uncertainties in this correction factor, especially in the case of the direction parallel to the seed long axis, photon spectra from the seed free in air was measured with a Si(Li) detector with the long axis of the seed parallel and perpendicular to the 1.3 m seed-detector distance. In this way it was possible to take into account significant differences in self absorption at different angles from the $^{145}$Sm seed which resulted from the low energy polychromatic photon spectrum.

At distances less than 8 mm from the seed, it is necessary to consider the significant contributions delivered by $\beta-$ particles from Eu impurities. The contributions to absorbed dose from $^{155}$Eu $\beta-$ particles is negligible due to self-absorption in the seed, as these electrons have maximum energies ranging between 100 keV and 246 keV. Among the $^{154}$Eu $\beta-$ particles, only those with average energy 695 keV have a significant contribution to the absorbed dose. The $\beta-$ source was also simulated with a regularly spaced array of point sources, 3 mm long. The absorbed dose rate around each point $^{154}$Eu source was calculated using the data by Radzievsky et al. [*Int. I. Appl. Radiat. Isot.*, 31, 431–436 (1980)] for point sources in water, with appropriate scaling for the differences in material. In these calculations, perturbation of the $\beta-$ field from the seed itself was not taken into account.

Within the distance of from 0.5 to 10 cm from the surface of the seed, more than 80% of the absorbed dose was due to photons with energy less than 62 keV. For 60 keV photons, the range of the ejected electrons is about 0.05 mm, which justifies Berger's assumption that energy transferred from photons to electrons of the medium is absorbed locally.

Measured Dose Distribution

The validity of the calculated dose distribution was examined experimentally for points in the plane defined by the perpendicular bisector. Lithium fluoride thermoluminescent dosimeters (TLD-700 rods, 1 mm×1 mm×6 mm) obtained from Harshaw Chemical Company, Cleveland, Ohio 44106 were inserted in a number of parallel holes in a 20 cm×20 cm×15 cm phantom made from A-150 plastic. The reason that A-150 was chosen is its similarity to soft tissue with respect to the photon linear attenuation coefficient and energy absorption coefficient. In the central hole of the phantom, a $^{145}$Sm seed was inserted in such a way that its center was at the same level as the center of each dosimeter. In the case of small distances from the source, the average absorbed dose to the entire volume of the dosimeter is significantly smaller than that at its center. A correction factor, k(r), was calculated assuming a 3 mm long linear source and a 6 mm long linear detector, taking into account the dependence of self-absorption at each angle and the tabulated build-up factors by Berger. The absorbed dose rate, D(r), in A-150 plastic at a distance r from the center of the seed and perpendicular to its long axis at its center, was evaluated using the relation:

$$\dot{D}(r) = k(r)\ (\mu/\rho)_{en}^{A/T} \frac{\dot{TL}_{Sm}}{\dot{TL}_{Co}} \dot{D}_{Co}$$

where $TL_{Sm}$ and $TL_{Co}$ are the rate of accumulation of the stored thermoluminescent signals in the $^{145}$Sm field and in a reference $^{60}$Co$\gamma$ field, which causes an absorbed dose rate in the TLD, $\dot{D}_{Co}$, and $(\mu/\rho)_{en}^{A/T}$ is the kerma-averaged ratio of the mass absorption coefficient in A-150 and in TLD material.

The factor $(\mu/\rho)_{EN}^{A/T}$ is an energy dependent parameter ranging from 0.76 for 30 keV photons to 1.00 for 65 keV. For this reason, the possible variation of the photon spectral shape with distance has to be taken into account. In the A-150 phantom the TLD-700 dosimeters (LiF:Mg,Ti, . . . ) were replaced with TLD-200 dosimeters ($CaF_2$:Dy, 1 mm×1 mm×6 mm) and the ratio "λ" of the absorbed dose rate in the two kinds of TLDs was measured at each location. Due to the difference between the atomic number of Ca and Li, the ratio of the absorbed dose rates in the two kinds of dosimeters changes drastically with photon energy in a low energy photon field. This change is by a factor of 2 for 30 and 65 keV photons. In the present case the ratio λ was found to be practically constant for distances greater than 4 mm. Thus there is no significant change in the shape of the photon spectrum with distance and a constant value of $(\mu/\rho)_{en}^{A/T}$ can be used. This result also justifies the use of constant interaction coefficients at these distances in the theoretical calculations. The neglibible variation of the photon energy spectrum with distance can be explained by the fact that in the energy range of interest, most of the energy transfer from the photon field to the phantom takes place through the photoelectric interaction. Further, the main consequence of Compton interactions is scattering rather than energy transfer. Another factor is the relative contribution to absorbed dose rate from impurity-produced higher energy photons at large distances (9% at 1 cm and 16% at 10 cm).

At distances smaller than about 4 mm the experimental verification of the theoretical calculations is very difficult due to the finite dimensions of the dosimeter and perturbations of the ($\beta-,\gamma$) field caused by the dosimeter itself. The following experimental technique was used in order to get a rough idea of the validity of the theoretical calculations. Dosimeters (TLD-700 and TLD-200) were put in contact with the seed with their long axis parallel to that of the seed. The ratio "λ" of the average absorbed dose rate in the volume of each kind of dosimeter was determined. It was assumed that the thermoluminescent efficiency of both kinds of dosimeters in the mixed ($\beta-,\gamma$)$^{145}$Sm field is the same as that in the reference $^{60}$Co $\gamma$ field, i.e. the amount of the emitted thermoluminescent light per unit imparted energy from photons and from beta particles is identical, irrespective of their energy distribution, at doses smaller than 1.4 Gy. The ratio "λ" in the case of close contact, 6.7±0.3 (1 SD), was significantly lower than the value of 9.7±0.3 found at distances between 1 cm and 4 cm. The photon spectra in these cases are practically identical; thus the difference in the ratio "λ" is due to the action of the beta particles. According to these experimental results the $\beta-$ contribution to the average absorbed dose in the TLD-700 volume was (33±8)% of the total, while according to the theoretical calculations it was 26%.

EXAMPLE 4

Source Strength and Purity of Sm-I45 Sources

Irradiation of 1 mg of $Sm_2O_3$ with $8.7\times10^{20}$n/cm$^2$ provided 1.5 mCi of $^{145}$Sm, with less than 2% of $^{154,155}$Eu impurities as determined spectroscopically. The measured photon energy spectra for a $^{145}$Sm seed (Ge detector) is shown in FIG. 1. No significant contamination from impurities is present, as also was the case for surveys of the spectra beyond 1 MeV. The measured impurities of 2.0% $^{154}$Eu and 0.7% $^{155}$Eu (relative to $^{145}$Sm activity at end of bombardment) contributes less than 10% of the dose within a few cm of the source, although this contribution will increase during the life of the source ($T_{\frac{1}{2}}$of $^{154}$Eu=8.5 y). Trace amounts of $^{156}$Eu were found after irradiations of $^{144}$Sm metal, but none was found with the $Sm_2O_3$ sources when measured 6 months post irradiation.

Source strengths of ~112 MBq (3 mCi) were produced in order to evaluate dosimetric parameters and to facilitate biological measurements in cell culture and small animals. Application as temporary brachytherapy implants would presumably require higher activity sources, similar to $^{125}$I seeds provided commercially for therapy (up to 40 mCi). The measured dose rates at 1 cm of ~0.015 Gy/hr·37 MBq (1.5 rads/h.mCi) for $^{145}$Sm is similar to that reported for $^{125}$I, Thirty to 40 mCi sources could be produced by increasing the irradiation time, using a higher incident fluence rate, and/or through the use of Sm metal rather than the oxide used here.

EXAMPLE 5

Dosimetry of Sm-145 Sources

Figure 2:
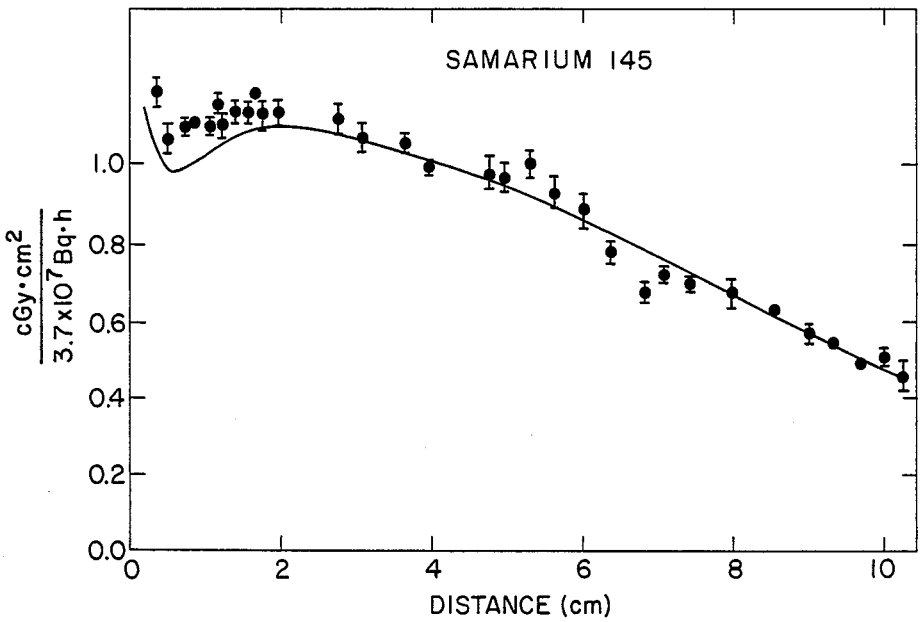
FIG. 2 plots the dose distribution in "tissue equivalent" A-150 plastic phantom ($20\times20\times15$ mm). Measured values are given by data points, $\neq$SD while the solid line represents the calculated values.

FIG. 2 presents the theoretical and experimental results for the absorbed dose rate per unit activity of $^{145}$Sm at the plane perpendicular to the long axis of the seed at its center. Error bars correspond to 1 standard deviation. In FIG. 2 the absorbed dose rate in A-150 plastic was multiplied by the square of the distance, $r^2$, in order to remove geometrical attenuation and to allow convenient presentation of the results. The agreement between the experimental and the theoretical data is generally good with respect to the existing errors (the main source of systematic error is the 4.5% total relative error in the determination of the absorbed dose rate to the dosimeters in the $^{60}$Co $\gamma$ calibration field). At distances smaller than 2.5 cm the experimental data are approximately 5% higher than the theoretical.

Figure 3:
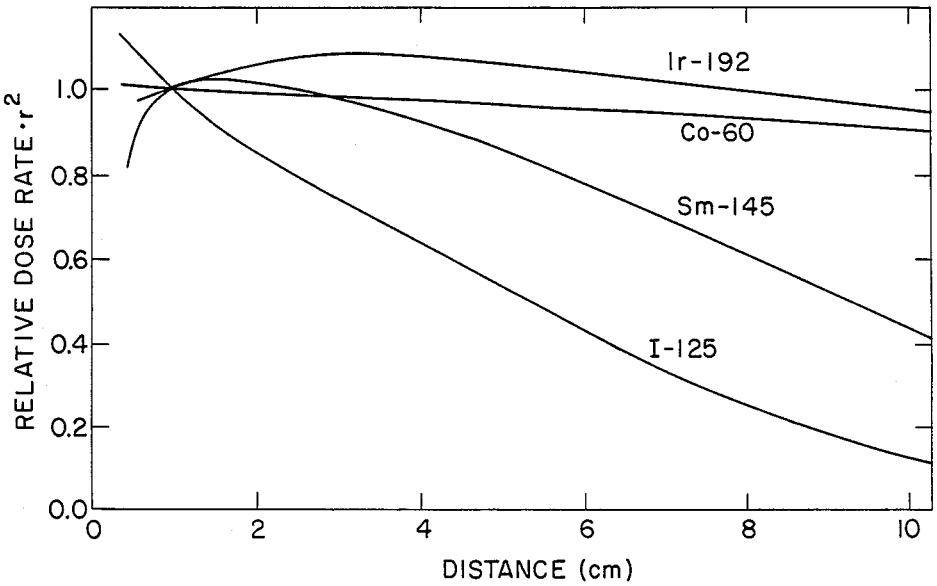
FIG. 3 plots the dose distribution for various conventional brachytherapy sources, compared to $^{145}Sm$ (normalized at 1 cm).

For comparison, results from absorbed dose measurements with the $^{145}$Sm seed are replotted in FIG. 3, along with corresponding data (normalized at 1 cm) for three other widely used brachytherapy sources. Included in FIG. 3 are a low energy photon source, $^{125}$I; a medium energy source, $^{192}$Ir; and a high energy $^{60}$Co source.

The reduction of the absorbed dose rate in soft tissue at distances larger than 2 cm around $^{145}$Sm is such that it may fill the existing gap between the medium and the high photon energy sources (such as $^{192}$Ir, $^{226}$Ra, and $^{60}$Co) and the low photon energy sources (such as $^{125}$I, and $^{103}$Pd). This characteristic may be desirable in many clinical situations; the use of $^{145}$Sm seeds rather than higher photon energy sources may reduce the absorbed dose of organs at risk outside the target volume (such as the rectum, bladder and uterus) while reducing the number of required sources (relative to $^{125}$I) for large tumors in intracavitary gynecological therapy. Another possible advantage of $^{145}$Sm over $^{125}$I seeds is that with similar construction, attenuation in the encapsulation should be smaller, thus reducing problems generated by significant anisotropy in absorbed dose rate around $^{125}$I seeds. Further enhancement of absorbed dose in osseous tissues close to the treatment volume may also be reduced, relative to that from $^{125}$I seeds.

We claim:

1. An implantable radiation source comprising a samarium-145 source encapsulated into a titanium tube.

* * * * *